United States Patent [19]
Hemker et al.

[11] Patent Number: 6,100,050
[45] Date of Patent: Aug. 8, 2000

[54] FACTOR VIII:CA CHROMOGENIC ASSAY

[75] Inventors: Hendrik Coenraad Hemker; Hendricus Johannes Kessels; Suzette Lucette BeGuin, all of Maastricht, Netherlands

[73] Assignee: Dade Behring AG, Dudingen, Switzerland

[21] Appl. No.: 08/781,079

[22] Filed: Jan. 9, 1997

Related U.S. Application Data

[63] Continuation of application No. 08/140,331, Sep. 30, 1993, abandoned, which is a continuation of application No. 07/553,219, Jul. 12, 1990, abandoned, which is a continuation-in-part of application No. 07/394,822, Aug. 17, 1989, abandoned.

[51] Int. Cl.$^7$ .................................................. C12Q 1/56
[52] U.S. Cl. ............................. 435/13; 435/217; 435/219
[58] Field of Search ............................. 435/13, 23, 24, 435/214, 69.2, 217, 219, 810; 436/69

[56] References Cited

U.S. PATENT DOCUMENTS

| | | | |
|---|---|---|---|
| 5,308,756 | 5/1994 | Van de waart | 435/13 |
| 5,506,112 | 4/1996 | Lang et al. | 435/13 |

FOREIGN PATENT DOCUMENTS

| | | |
|---|---|---|
| 0496723 | 1/1992 | European Pat. Off. . |
| WO9201229 | 1/1992 | WIPO . |

OTHER PUBLICATIONS

Wagenvoord R., Development of a Simple Chromogenic Factor VIII Assay . . . Haemostasis 1989 19: 196–204.
Pieters J., In Situ Generated Thrombin is the Only Enzyme . . . Blood vol. 74 No. 3 1989 pp. 1021–1024.
Wagenvoord R., Development of a Sensitive & Rapid Chromogenic Factor IX Assay . . . Haemostasis 1990: 20 276–288.
Van Dieijen G., Assembly of the Intrinsic Factor X Activating Complex . . . Thromb Haemo 53 (3) 396–400 1985.
Kessels H., A Method For Measuring Activated Factor VIII in Plasma, Thromb Haemost 66 (4) 430–434 1991.
Wagenvoord, R., Hendrix H., Hemker, H., Development of a Simple Factor VIII Assay for Clinical Use, (Abstract), Thrombosis Haemostasis; 58:p.341 (1987).
Scandinavian Journal of Haemotology, Supplement No. 40, vol. 33 (1984)(Copenhaen, DK) Rosen: "Assay of factor VIII:C with a chromogenic substrate", pp. 139–145.
Haemostasis, vol. 17, No. -2, Jan.–Apr. 1987, Karger AG, (Basel, CH), G. Van Dieijen et al.: "Spectrophotometric Method for the assay of human blood coagulation factor VIII", pp. 14–24.
Biochemistry, vol. 19 No. 3, Feb. 5, 1980, American Chemical Society, (Washington, US), G.A. Vehar et al.: "Preparation and properties of bovine factor VIII (antihemophilic factor)", pp. 401–410.
Biochem. vol. 11 (1972) Fujikawa et al.: Bovine Factor XI (Stuart Factor) Mechanism of activation by Russel's Viper Venom, 4892.

*Primary Examiner*—Ralph Gitomer
*Attorney, Agent, or Firm*—Cynthia G Tymeson; Louise S Pearson; Lois K Ruszala

[57] ABSTRACT

A chromogenic assay for determination of blood coagulation Factor VIII:Ca, using an indicator of Factor Xa simultaneously as a measure of Factor VIII:Ca concentration and as an inhibitor of Factor Xa. This technique can be applied to measure the concentration of an activating enzyme using the rate of conversion of the indicator molecule of the product of that enzyme as an indirect indicator of enzyme concentration.

22 Claims, No Drawings

FACTOR VIII:CA CHROMOGENIC ASSAY

This is a continuation of application Ser. No. 08/140,331, filed on Sep. 30, 1993, now abandoned, which is a continuation of application Ser. No. 07/553,219, filed on Jul. 12, 1990, now abandoned, which is a continuation-in-part of application Ser. No. 7/394,822 filed Aug. 17, 1989, now abandoned. This invention relates generally to the field of chromogenic assays and more specifically to a chromogenic assay for the determination of levels of the blood coagulation factor VIII:Ca contained in plasma.

BACKGROUND OF THE INVENTION

Clot formation in plasma is initiated by the serial enzymatic activation of clotting factors, which results in the appearance of small traces of thrombin. Hurlet-Birk Jensen A., et al. *Factor V and VIII Activation "In Vivo" during Bleeding. Evidence of Thrombin Formation at the Early Stage of Hemostatasis.* Path. Biol. 1976; 24, p.6–10. The explosive nature of the coagulation process is a consequence of the position feedback reactions that these thrombin traces exert on the cofactors V. Colman, R W, *The Effect of Proteolytic Enzymes on Bovine Factor VI. Kinetics of Activation and Inactivation by Bovine Thrombin,* Biochem. 1969; 4: p.1438–1444, Lindhout, M J, *Activation of Bovine Factor V by Thrombin and a Protease from Russell's Viper Venom (RVV),* Thromb. Haemost. 1979; 42: p.491. Rapaport, S I, et al., *Further Evidence That Thrombin Activation of Factor VIII is an Essential Step In Intrinsic Clotting,* Scand J. Clin. Lab. Invest. 1965; 17: p.84–88, Biggs, R., et al. *Thrombin and the Interaction of Factors VIII and IX,* Brit J. Haemat. 1965; 11: p.276–295, Hemker, H C, et al., *Reaction Sequence of Blood Coagulation,* Nature 1967; 215: p.1201, Osterud, B., et al., *Formation of Intrinsic Factor X Activator With Special Reference to the Role of Thrombin,* Br. J. Haematol 1971; 21: p.643–660, Hultin, M B, et al., *Activation of Factor X by Factors IXa and VIII; A Specific Assay for Factor IXa in the Presence of Thrombin-Activated Factor VIII,* Blood 1978; 52: p.928–940, and on platelets, Davey, M G, et al., *Actions of Thrombin and Other Proteolytic enzymes on Blood Platelets,* Nature 1967; 216: p.857–858. Activated Factors V and VIII:C dramatically boost the performance of Factors Xa and IXa, whereas activated platelets provide, among other things, the negatively charged surface necessary for most coagulation reactions. Bevers, E M, et al., *Generation of Prothrombin Converting Activity and the Exposure of Phosphatidylserine at the Outer Surface of Platelets,* Eur. J. Bioch. 1982; 122: p.429–436.

According to prior methods Factor VIII:C concentrations, and also Factor VIII:C activation in plasma were measured using coagulation assays, involving VIII:C deficient plasma. Soulier, P., et al., *Deficit En Beme Facteur Prothromboplastique plasmatique, Rapports Entre le PTA et le Facteur Hageman,* Thrombin. Diathes. Haemorrh. 1958; 2: p.1, Rappaport, S I, et al., *A Simple Specific One-Stage Assay for Plasma Thromboplastin Antecedent Activity,* J. Lab. Clin. Med. 1961; 57: p.771, Hardisty, R M et al., *A One-Stage Factor VIII (Antihemophilic Globulin) Assay and Its Uses on Venous and Capillary Plasma,* Thrombos, Diathes, Haemorrh. 1962; 7: p.215, Veltkamp, J J, et al., *Detection of the Carrier State in Hereditary Coagulation Disorders,* Thrombos, Diathes. Haemorrh. 1968; 19: p.279–303 and 403–422, Suomela, H, et al. *The Activation of Factor X Evaluated by Using Synthetic Substrates,* Thromb. Res. 1977; 1: p.267–281, Van Dieijen, G, et al., *The Role of Phospholipid and Factor VIIIa in the Activation of Bovine Factor X,* J. Biol. Chem. 1981; 256: p.3433–3442. The occurrence of various feedback reactions, however, made it impossible to relate, in a quantitatively reliable way, these values to the amounts of activated VIII:Ca. The advent of a chromogenic substrate for Factor Xa, and the recognition that a property of activated Factor VIII:Ca is accelerated activation of Factor X by IXa, phospholipids and calcium ions made a more direct method of determining functional Factor VIII:Ca conceivable. Suomela, H, et al. Supra, Van Dieijen, et al., *The Role of Phospholipid and Factor VIIIa in the Activation of Bovine Factor X,* J. Biol. Chem. 1981; 256: p.3433–3442. Still, feedback reactions of Factor Xa on Factor VIII:C, and the inactivation of Factor Xa by the antithrombin III and α1-antitrypsin present in plasma, threatened to seriously hamper the feasibility of such a Factor VIII:Ca assay in plasma. Vehar, G A, et al., *Preparation and Properties of Bovine Factor VIII (Antihemophilic Factor),* Biochemistry 1980; 19: p.401–410, Hultin, M B, *Role of Human Factor VIII in Factor X Activation,* J. Clin. Invest. 1982; 69: p.950–955, Lollar, P, et al., *Activation of Porcine Factor VIII:C by Thrombin and Factor Xa,* Biochemistry 1985; 24: p.8056–8064, Neuenschwanter, P, et al., *A Comparison of Phospholipid and Platelets in the Activation of Human Factor VIII by Thrombin and Factor Xa, and in the Activation of Factor X,* Blood 1988; 72: p.1761–1770, and Factor X, Jesty, J., et al., *The Mechanism of Activation of Factor X,* J. Biol. Chem. 1974; 249: p.5614–5622. On the basis of a method by Pieters et al., *In Situ Generated Thrombin is the Only Enzyme that Effectively Activates Factor VIII:C and Factor V in Plasma,* Blood, in press (hereby incorporated by reference), we developed a scheme for measuring Factor VIII:Ca in plasma, that circumvents these difficulties.

The classical method for the determination of Factor VIII:Ca activity in plasma estimates the activity of the clotting factor in a plasma sample from the amount of time by which it shortens the prolonged clotting time of a plasma cogenitally deficient in that factor, as compared to a normal plasma. As there is no solid theoretical basis that underlies the relationship between the coagulation time and the percentage of coagulation factor activity, these assays are bioassays in the sense that the activities have to be read from a standard curve, and that the values of these activities are only valid with respect to the method by which they are measured. Consequently, a need exists for a more quantitative method to measure Factor VIII:Ca.

SUMMARY OF THE INVENTION

This invention provides a highly sensitive, reproducible, and convenient assay for determination of the levels of blood coagulation Factor VIII:Ca contained in blood serum, plasma, and other fluids. Since Factor VIII:Ca is not an enzyme, its functional concentration cannot be measured directly by way of a chromogenic substrate. Instead, the ability of Factor VIII:Ca to enhance Factor X activation in the presence of Factor IXa, phospholipids, and $Ca_{2+}$, is exploited. Factor Xa concentration can be determined chromogenically, which permits a quantitative estimation of the Factor VIII:Ca a level.

In the assay of this invention, a test sample of blood serum, plasma, or other Factor VIII:Ca containing fluid is added to a solution containing activated blood coagulation Factor IXa, and calcium ions and phospholipid. Factor X is added to the mixture. Factor IXa and Factor VIII:Ca act to accelerate the conversion of the Factor X, a zymogen, to activated Factor X, (hereafter referred to as Factor Xa). An indicator agent is added to the reaction mixture, which reacts with the Factor Xa so formed, to release a signal molecule, which may be conveniently measured. The following equations further illustrate the steps of the present method:

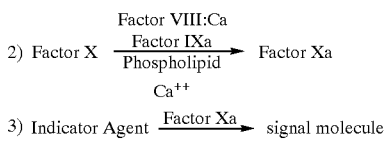

In accordance with the method of this invention, an assay is provided which has a high degree of sensitivity and reproducibility for Factor VIII:Ca concentration. Another object of this invention is to provide a kit for the convenient performance of routine laboratory assays of Factor VIII:Ca containing fluids. A further object of this invention is to provide an assay for Factor VIII:Ca which is not affected by the presence of heparin and other blood clot interactive substances. A still further object of this invention is to provide a bulk source of assay components to facilitate the operation of automated equipment capable of processing for assay large numbers of test samples. It is another object of this invention to suppress side reaction of Factor Xa that might distort the correlation. To that end it was found that inhibition of these side reactions can be obtained by using a high concentration of chromogenic substrate for Factor Xa.

This assay methodology may be applicable to the measurement of other activated factors; in particular e.g. Factor V. An activating enzyme (Enzyme A, i.e. the Factor IXa—factors VIII:Ca—phospholipid complex), is measured by indirectly measuring the rate of activation of an enzyme that is its natural substrate. The enzyme that results from this activation (Enzyme B) is allowed to act immediately on an indicator molecule. By its reaction with the indicator molecule (the concentration of which must suffice to saturate enzyme B) complicating reactions involving enzyme B are inhibited. (i.e. example, the activation of Factor VIII:C by Factor Xa, and the inhibition of Factor Xa by antithrombin III). Because enzyme B increases linearly in time, the signal molecule is produced according to a parabolic curve. The slope of the first derivative of this parabola is proportional to the concentration of enzyme A.

The advantages and performance of the present invention will be better understood by reference to the following detailed description and Example.

DETAILED DESCRIPTION OF THE PREFERRED EMBODIMENT

The method of the assay of the present invention comprises the steps of:

1. Combining a sample and a solution containing a sufficient amount of Factor IXa to saturate substantially all Factor VIII:Ca in said sample; a sufficient amount of a thrombin inhibitor to inhibit thrombin activity without affecting Factor Xa activity, a sufficient amount of phospholipids, calcium ion to facilitate the conversion of Factor X to Factor Xa.
2. Adding to the mixture a sufficient amount of Factor X to saturate substantially all of the complex of Factor IXa, Factor VIII:Ca and phospholipid.
3. Adding to the mixture a sufficient amount of an indicator agent capable of reacting with Factor Xa, said quantity of indicator agent being sufficient to suppress Factor Xa side reactions, to release a signal molecule; and
4. Measuring the signal molecule.

The foregoing method may be exemplified by reference to the following equations:

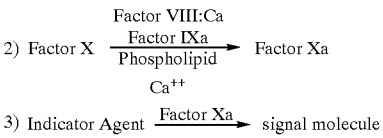

In practicing the method of the present invention, Factors IX and X may be obtained from virtually any animal or human source, and may be prepared by any fractionation or concentration method known to the art. In addition, a highly purified source of such factors is from recombinant vectors propagated in suitable host cell lines. One advantage to using factors from animal or recombinant vector sources is assurance that the product factors will not be contaminated with human pathogens such as hepatitis A and B, HTLV-III, or other such viruses. In the preferred embodiment of the present method, blood coagulation factors are of bovine origin.

It should be noted that because the sample undergoes a considerable dilution in the assay mixture (30 to 100 fold), the endogenous Factor IX concentration will very probably not be high enough to saturate all Factor VIII:Ca (up to 1 U/ml) present in the sample on Factor IXa, which is necessary for a reliable assay. Thus, a sufficient amount of Factor IXa must be added.

The conversion of Factor X to Xa proceeds most efficiently in the presence of phospholipids. These phospholipids may be such representative compounds as phosphotidyl choline, phosphotidyl serine, or cholesterol and mixtures thereof in various proportions. Other lipid and phospholipid compositions may be substituted as well.

It is our experience that optimal results are obtained with vesicles of 20 mole-% phosphatidyl serine and 80 mole-% phosphatidyl choline. This is not critical however; the ranges of acceptable composition are 5 to 40 mole-% phosphatidyl serine, 0 to 20 mole-% cholesterol, and 50–90 mole-% of phosphotidyl choline.

Any chemical source of calcium cation may be used to effectuate the conversion of Factor X. Sufficient calcium ion may be added to the original incubation mixture to drive the reaction converting Factor X to Factor Xa, or a second amount of calcium ion may be added at the time Factor X is to be converted. While the source of calcium cation ($Ca^{++}$) may be $CaCl_2$, $Ca(NO_2)_2$, $CaSO_4$, or other inorganic calcium cation containing compounds, the preferred source is $CaCl_2$.

A thrombin inhibitor is used to block thrombin activity on chromogenic substrate for Factor Xa. Useful thrombin inhibitors include α-NAPAP and hirudin.

In performing the assay of this invention, great variations in protein concentrations, incubation times, reagent concentrations, and temperatures may be employed. The selection of particular assay parameters will be influenced by the source, type, and size of the sample to be assayed, the anticipated levels of Factor VIII:Ca contained therein, and the threshold of sensitivity desired. Taking these circumstances into account, selection of assay parameters will be apparent to those skilled in the art. The parameters of the assay, which will enable anyone skilled in the art to carry out the assay in accordance with a preferred embodiment are set forth in the Example which follows.

It should be noted that, although the rate of Factor X activation is linearly proportional to the level of Factor VIII:Ca, the rate of amidolysis of the chromogenic substrate is not. In fact, the relation between absorbance and Factor VIII:Ca concentration is a second order polynomial. Because of this, at least two points are needed for a determination of the Factor VIII:Ca concentration. We found that best results are obtained when absorbance is measured continuously in time. The resulting curve is then analyzed by way of a second order least squares fit procedure. This yields the parameters A, B and C (equation: $A+B.t+C.t^2$). C is proportional to Factor VIII:Ca concentration.

Accordingly, an optional additional step in the present assay consists of adding a quenching agent to the incubation mixture at a fixed point in time after commencement of the reaction converting Factor X to Factor Xa. The quenching composition may be any substance capable of disrupting a protein-mediated chemical reaction, but the preferred composition is a buffered solution comprised of Tris, ethylenediaminetetracetic acid, sodium chloride, and sodium azide.

The blood coagulation factors of the present assay and the Factor VIII:Ca protein to be assayed are fragile functional proteins, and desirably a stabilizing substance of substances may be included during the incubation to optimize assay conditions and to protect functionality of assay components. Such stabilizing substances also protect functionality during storage wherein the assay components are maintained in either a wet or lyophilized state. Various stabilizers are known in the art; the preferred substances being polyethylene glycol and bovine serum albumin, either singly or in combination.

The indicator agent of the present invention is a molecule capable of reacting with blood coagulation Factor Xa. In such reaction, by-products of chemical reaction must be generated which produce a measurable signal moiety, U.S. Pat. Nos. 4,480,030 and 4,666,831 describe a class of chromogenic compounds capable of reacting with Factor Xa. The indicator CH OCO-D-CHG-Gly-Arg-pNA-AcOH (Pentapharm, Basel, Switzerland), is preferred. Upon reaction with Factor Xa, a signal molecule P-nitroaniline is released, which may be conveniently measured by spectrophotometric determination at 405 nm.

Other chromogenic indicator agents which are applicable with the present invention are available also. From the preceding disclosure it will be apparent to those skilled in the art that the signal moiety of the target indicator agent may be radiolabelled, preferably by tritium or carbon 14, and the signal molecule upon release can be isolated by exclusion chromatography, dialysis, immunoadsorption, or other convenient separation techniques. Radiolabelled indicator agents, while more cumbersome to use, have the advantage of greater sensitivity in those situations wherein unusually great sensitivity is needed.

It is contemplated within the scope of the present invention that the components of the Factor VIII:Ca assay may be available as a kit for the convenient and routine performance of a large number of such assays.

A kit for performing a Factor VIII:C assay on a sample comprising: a) a first vessel containing: a sufficient amount of Factor IXa to saturate all Factor VIII:Ca in said sample, a sufficient amount of a thrombin inhibitor to inhibit thrombin activity without affecting Factor Xa activity, a sufficient amount of phospholipid and calcium ion to facilitate the conversion of Factor X to Factor Xa; b) a second vessel containing a sufficient amount of Factor X to saturate the complex of Factors IXa and VIII:C and phospholipid; c) a third vessel containing a sufficient quantity of an indicator agent capable of reacting with Factor Xa, said quantity of indicator agent being sufficient to suppress Factor Xa side reactions. An optimal fourth vessel can be included with a quenching composition.

To optimize shelf life of the components of the kit it is desirable to lyophilize them in the aforementioned vessels. The said components may be readily reconstituted by adding water at the time assays are to be performed. The vessels containing assay components are readily adapted to automated assay equipment.

EXAMPLE 1. FACTOR VIII:Ca GENERATION IN THROMBOPLASTIN ACTIVATED PLASMA

Factor VIII:Ca generation is triggered by addition of 10 $\mu$l of a solution of $CaCl_2$ (167 mM) containing human brain thromboplastin (dilution 1/18) to 90 $\mu$l of defibrinated plasma. At various times aliquots of this mixture are taken for assay of the Factor VIII:Ca concentration. Each aliquot is diluted 100 fold in a cuvette containing Factor IXa (100 nM), phospholipid vesicles (20 $\mu$M, 20 mole-% phosphatidyl serine/80 mole-% phosphatidyl choline), $CaCl_2$ (5 mM) and —NAPAP (1 $\mu$M), in buffer at 37° C. After 10 seconds, Factor Xa chromogenic substrate ($CH_3OCO\_D\_CHG$-Gly-Arg-Pna-AcOH; Pentapharm, Basel Switzerland) is added to the cuvette so as to obtain a concentration of 400 $\mu$M. Factor X activation is started after another 10 seconds by addition of Factor X, to a concentration of 0.33 $\mu$M. Concentrations mentioned are final, i.e. they are obtained after all additions to the cuvette have been made. The course of absorbance at 405 nm is then measured continuously in time.

The build up of absorbance in time is governed by the following equation:

$$A(t).=A_0+k1\cdot[x_a]_0\cdot t+k2\cdot[\text{VIII:Ca}], t$$

The quadratic term which is a function of the Factor VIII:Ca concentration is estimated from the absorbance-time curve by way of a quadratic least squares fit procedure. From this the Factor VIII:Ca concentration is inferred, using a value for k2 of 1.164 $mA/min^2/\%VIII:ca$, which has been determined previously.

Factor VIII:Ca concentrations at each time point, stated as a percentage of the total Factor VIII:C, are shown in the table below.

TABLE 1

| Time (min) | [VIII:Ca] (%) |
|---|---|
| 0.50 | 0.7 |
| 1.00 | 2.9 |
| 1.25 | 10.1 |
| 1.50 | 44.1 |
| 1.75 | 73.8 |
| 2.00 | 62.1 |
| 2.25 | 49.7 |
| 2.75 | 39.8 |

What is claimed is:

1. A kit for performing a Factor VIII:Ca assay of a sample comprising:
   a) a first vessel containing a sufficient amount of Factor IXa to saturate all Factor VIII:Ca in said sample, a sufficient amount of a thrombin inhibitor to inhibit thrombin activity without affecting Factor Xa activity, a sufficient amount of phospholipid and calcium ion to facilitate the conversion of Factor X to Factor Xa;

b) a second vessel containing Factor X in an amount sufficient to saturate a complex of Factors IXa and VIII:Ca and phospholipid; and c) a third vessel containing a sufficient quantity of an indicator agent that reacts with reacting with Factor Xa, said quantity of indicator agent being sufficient to suppress Factor Xa side reactions.

2. The kit of claim 1 where Factors IXa and X are of bovine origin.

3. The kit of claim 1 wherein the phospholipid is comprised of between 5 to 40 mole-% phosphatidyl serine, 0 to 20 mole-% cholesterol and 50–90 mole-% of phosphotidyl choline.

4. The kit of claim 1 wherein the phospholipid is comprised of 20 mole-% of phosphatidyl serine and 80 mole-% phosphatidyl choline.

5. The kit of claim 1 wherein the indicator is selected from the group consisting of enzymatic, radiometric, fluorescent or chromogenic indicators.

6. The kit of claim 1 wherein said indicator is chromogenic.

7. A kit for performing a Factor VIII:Ca assay on a sample comprising:

a) a first vessel containing a sufficient amount of Factor IXa to saturate all Factor VIII:Ca in said sample, a sufficient amount of a thrombin inhibitor to inhibit thrombin activity without affecting Factor Xa activity, a sufficient amount of phospholipid and calcium ion to facilitate the conversion of Factor X to Factor Xa;

b) a second vessel containing Factor X in an amount sufficient to saturate the complex of Factors IXa and VIII:Ca and phospholipid;

c) a third vessel containing a sufficient quantity of quenching agent to stop the conversion of Factor X to Factor Xa; and d) a fourth vessel containing a sufficient quantity of an indicator agent that reacts with reacting with Factor Xa, said quantity of indicator agent being sufficient to suppress Factor Xa side reactions.

8. The kit of claim 7 where Factors IXa and X are of bovine origin.

9. The kit of claim 7 wherein the phospholipid is comprised of: between 5 to 40 mole-% phosphatidyl serine, 0 to 20 mole-% cholesterol and 50–90 mole-% of phosphotidyl choline.

10. The kit of claim 7 wherein the phospholipid is comprised of 20 mole-% of phosphatidyl serine and 80 mole-% phosphatidyl choline.

11. The kit of claim 7 wherein the said indicator is selected from the class consisting of: enzymatic, radiometric, fluorescent or chromogenic indicators.

12. The kit of claim 7 wherein said indicator is chromogenic.

13. The kit of claim 7 wherein said quenching agent is any substance capable of disrupting a protein-mediated chemical reaction.

14. The kit of claim 13 wherein the quenching substance is a buffered solution of Tris[hydroxymethyl]aminomethane, ethylenediaminetetraacetic acid, sodium chloride and sodium azide.

15. A method for determining the concentration of blood coagulation Factor VIII:Ca in a fluid sample comprising:

a) combining said fluid sample with a sufficient amount of Factor IXa to saturate substantially all Factor VIII:Ca in said sample; a sufficient amount of thrombin inhibitor to inhibit thrombin activity without affecting Factor Xa activity in the presence of a sufficient amount of calcium ions and phospholipid to facilitate the conversion of Factor X to Factor Xa;

b) adding a sufficient amount of Factor X to saturate the complex of Factors IXa and VIII:Ca and phospholipid;

c) adding a sufficient quantity of an indicator agent capable of reacting with Factor Xa, to release a signal molecule, said quantity of indicator agent being sufficient to suppress Factor Xa side reactions; and d) measuring the released signal molecule and correlating the measurement of the signal molecule with the concentration of the Factor VIII:Ca in the sample.

16. The method of claim 15 further comprising adding a quenching substance after the addition of Factor X to prevent the conversion of Factor X to Factor Xa.

17. The method of claim 15 or 16 wherein Factors IXa and X are obtained from an animal source.

18. The method of claim 15 wherein Factors IXa and X are obtained from a recombinant vector propagated in a host cell line.

19. The method of claim 15 wherein the indicator agent is selected from the class consisting of enzymatic, radiometric, fluorescent and chromogenic indicators.

20. The method of claim 15 wherein said indicator agent is chromogenic.

21. The method of claim 20 wherein said indicator agent is CH OCO-D-CHG-Gly-Arg-Pna-AcOH.

22. A method for determining the concentration of Factor VIII:Ca in a bodily fluid sample said body fluid sample suspected of comprising both Factor VIII:Ca and Factor VIII:C, the method comprising: activating added Factor X to Factor Xa with the Factor VIII:Ca in the sample and suppressing the activation of Factor VIII:C in said sample to Factor VIII:Ca, measuring the rate of activation of Factor X to Factor Xa and correlating the Factor Xa activation rate to the concentration of the Factor VIII:Ca in the sample.

\* \* \* \* \*